(12) United States Patent
Shi

(10) Patent No.: US 12,148,072 B2
(45) Date of Patent: Nov. 19, 2024

(54) SYSTEMS AND METHODS FOR MEDICAL IMAGING

(71) Applicant: SHANGHAI UNITED IMAGING HEALTHCARE CO., LTD., Shanghai (CN)

(72) Inventor: Tingrong Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 353 days.

(21) Appl. No.: 17/804,595

(22) Filed: May 30, 2022

(65) Prior Publication Data
US 2022/0292738 A1 Sep. 15, 2022

Related U.S. Application Data

(63) Continuation of application No. PCT/CN2020/095281, filed on Jun. 10, 2020.

(30) Foreign Application Priority Data

Nov. 29, 2019 (CN) .......................... 201911207491.6

(51) Int. Cl.
*G06T 7/00* (2017.01)
*G06T 1/60* (2006.01)
(Continued)

(52) U.S. Cl.
CPC .............. *G06T 11/005* (2013.01); *G06T 1/60* (2013.01); *G06T 3/4038* (2013.01); *G06T 5/50* (2013.01);
(Continued)

(58) Field of Classification Search
CPC .... G06K 9/6228; G06K 9/6262; G06K 9/627; G06K 9/6276; G06K 9/629;
(Continued)

(56) References Cited

U.S. PATENT DOCUMENTS

2006/0212260 A1 9/2006 Kopelman et al.
2010/0220909 A1 9/2010 Thielemans et al.
(Continued)

FOREIGN PATENT DOCUMENTS

CN 101909165 A 12/2010
CN 102693533 A 9/2012
(Continued)

OTHER PUBLICATIONS

International Search Report in PCT/CN2020/095281 mailed on Sep. 16, 2020, 5 pages.
(Continued)

*Primary Examiner* — Quan M Hua
(74) *Attorney, Agent, or Firm* — METIS IP LLC

(57) ABSTRACT

The present disclosure provides a system and method for imaging. The method may include obtaining a plurality of protocols for scanning a subject using a scanner, wherein the plurality of protocols correspond to a plurality of regions of the subject, respectively. The method may also include determining one or more stitching parameters between protocols corresponding to each pair of neighboring regions of the plurality of regions. The method may further include generating image stitching verification data associated with the plurality of regions based at least in part on at least one of the one or more stitching parameters between protocols corresponding to each pair of neighboring regions of the plurality of regions. The method may still further include directing the scanner to scan the subject based at least in part on the image stitching verification data.

20 Claims, 10 Drawing Sheets

(51) Int. Cl.
  *G06T 3/4038* (2024.01)
  *G06T 5/50* (2006.01)
  *G06T 7/13* (2017.01)
  *G06T 7/174* (2017.01)
  *G06T 11/00* (2006.01)

(52) U.S. Cl.
  CPC ............... *G06T 7/13* (2017.01); *G06T 7/174* (2017.01); *G06T 2207/20212* (2013.01)

(58) Field of Classification Search
  CPC .......... G06K 9/00261; G06K 9/00288; G06K 9/00228; G06K 9/00268; G06K 9/00281; G06K 9/6202; G06K 2009/4666; G06K 9/00362; G06K 9/4642; G06K 9/6206; G06K 9/6255; G06K 9/6256; G06K 9/00275; G06K 9/00308; G06K 9/00926; G06K 9/3233; G06K 9/4671; G06K 9/6215; G06N 3/0454; G06N 3/084; G06N 3/08; G06T 11/00; G06T 2207/10016; G06T 2207/10024; G06T 2207/20081; G06T 2207/30201; G06T 2207/30241; G06T 2207/30244; G06T 7/251; G06T 7/74; G06T 7/80
  See application file for complete search history.

(56) References Cited

U.S. PATENT DOCUMENTS

| | | |
|---|---|---|
| 2013/0090946 A1 | 4/2013 | Foo et al. |
| 2014/0180060 A1 | 6/2014 | Parrish et al. |
| 2014/0348401 A1 | 11/2014 | Xu et al. |
| 2015/0164457 A1 | 6/2015 | Nett et al. |
| 2016/0012586 A1 | 1/2016 | Senegas et al. |
| 2016/0163115 A1 | 6/2016 | Furst |
| 2017/0103558 A1* | 4/2017 | Sharma .................. G06T 11/60 |
| 2017/0156630 A1 | 6/2017 | Gabr et al. |
| 2017/0311921 A1 | 11/2017 | Feuerlein et al. |
| 2018/0045800 A1 | 2/2018 | Nielsen et al. |
| 2019/0088361 A1* | 3/2019 | Ouyang .............. A61B 5/7435 |
| 2019/0122400 A1 | 4/2019 | Li et al. |
| 2019/0317239 A1* | 10/2019 | Olsson .............. G01C 21/3852 |
| 2019/0336097 A1 | 11/2019 | Bregman-Amitai et al. |

FOREIGN PATENT DOCUMENTS

| | | |
|---|---|---|
| CN | 103986872 A | 8/2014 |
| CN | 107802265 A | 3/2018 |
| CN | 109567843 A | 4/2019 |
| CN | 109692015 A | 4/2019 |
| CN | 109717885 A | 5/2019 |
| CN | 109924993 A | 6/2019 |
| CN | 110215228 A | 9/2019 |
| WO | 2016009309 A1 | 1/2016 |
| WO | 2021103481 A1 | 6/2021 |

OTHER PUBLICATIONS

Written Opinion in PCT/CN2020/095281 mailed on Sep. 16, 2020, 6 pages.

First Office Action in Chinese Application No. 201911207491.6 mailed on Jan. 27, 2022, 15 pages.

The Second Office Action in Chinese Application No. 201911207491.6 mailed on Nov. 11, 2022, 14 pages.

The Extended European Search Report in European Application No. 20892215.3 mailed on Apr. 3, 2023, 10 pages.

Shen, Tao, Research on Calibration Method and Interior Tomography of High Resolution CT, Master's Theses of School of Biological Science & Medical Engineering Southeast University, 2017, 83 pages.

Ouyang, Bin et al., Effect of CT Scanning and Reconstruction Parameters on the Quality of Imaging for Radiation Therapy, China Medical Herald, 14(1): 4-7, 2017.

\* cited by examiner

600

---

Obtaining a plurality of protocols for scanning a subject using a scanner, wherein the plurality of protocols correspond to a plurality of regions of the subject, respectively — 610

Determining one or more scanning parameters for each of the plurality of regions based on the plurality of protocols, and one or more stitching parameters between protocols corresponding to each pair of neighboring regions of the plurality of regions — 620

Generating image stitching verification data associated with the plurality of regions based on at least one of the one or more scanning parameters of each region and the one or more stitching parameters between protocols corresponding to each pair of neighboring regions of the plurality of regions — 630

Directing the scanner to scan the subject based at least in part on the image stitching verification data — 640

810 — Obtaining a plurality of protocols for scanning a subject using a scanner, wherein the plurality of protocols correspond to a plurality of regions of the subject, respectively 820 — Determining one or more scanning parameters for each of the plurality of regions based on the plurality of protocols, and one or more stitching parameters between protocols corresponding to each pair of neighboring regions of the plurality of regions 830 — Adjusting at least one of the one or more scanning parameters of at least one region or the one or more stitching parameters between protocols corresponding to at least one pair of neighboring regions according to a parameter adjustment instruction, and/or adding into or deleting from the plurality of protocols at least one according to a protocol modification instruction 840 — Generating image stitching verification data associated with the plurality of regions based on the adjusted at least one of the one or more scanning parameters of the at least one region, the adjusted one or more stitching parameters corresponding to the at least one pair of neighboring regions, and/or protocols after the at least one protocol is added into or deleted from the plurality of protocols.

850 — Directing the scanner to scan the subject based at least in part on the image stitching verification data

```
┌─────────────────────────────────────────────────────────────┐
│ Obtaining a plurality of protocols for scanning a subject  │  910
│ using a scanner, wherein the plurality of protocols        │
│ correspond to a plurality of regions of the subject,       │
│ respectively                                                │
└─────────────────────────────────────────────────────────────┘
                              │
                              ▼
┌─────────────────────────────────────────────────────────────┐
│ Determining one or more stitching parameters between       │  920
│ protocols corresponding to each pair of neighboring        │
│ regions of the plurality of regions                         │
└─────────────────────────────────────────────────────────────┘
                              │
                              ▼
┌─────────────────────────────────────────────────────────────┐
│ Generating image stitching verification data associated    │  930
│ with the plurality of regions based at least in part on    │
│ at least one of the one or more stitching parameters       │
│ between protocols corresponding to each pair of            │
│ neighboring regions of the plurality of regions             │
└─────────────────────────────────────────────────────────────┘
                              │
                              ▼
┌─────────────────────────────────────────────────────────────┐
│ Directing the scanner to scan the subject based at least   │  940
│ in part on the image stitching verification data            │
└─────────────────────────────────────────────────────────────┘
```

FIG. 9

SYSTEMS AND METHODS FOR MEDICAL IMAGING

CROSS-REFERENCE TO RELATED APPLICATIONS

This application is a continuation of International Application No. PCT/CN2020/095281, filed on Jun. 10, 2020, which claims priority to Chinese Application No. 201911207491.6, filed on Nov. 29, 2019, the contents of which are hereby incorporated by reference.

TECHNICAL FIELD

The present disclosure generally relates to medical imaging, and more particularly, relates to imaging systems and methods involving image stitching.

BACKGROUND

Medical imaging techniques including, e.g., magnetic resonance imaging (MRI), positron emission tomography (PET), computed tomography (CT), single-photon emission computed tomography (SPECT), etc., are widely used in clinical diagnosis and/or treatment. In a medical imaging process of a subject (e.g., a patient or a portion thereof), the subject may be scanned by a scanner. The scanning of the subject may be performed at a plurality of sessions corresponding to a plurality of regions of the subject according to, for example, a scanning plan if a size of the subject to be scanned exceeds a maximum field of view (FOV) of the scanner. After one or more images of each of the plurality of regions are obtained, a stitched image of the subject may be generated by stitching the one or more images of each of the plurality of regions in a certain manner. However, errors occur when the images of the plurality of regions are stitched into the stitched image of the subject since the plurality of regions are usually scanned using different scanning parameters. Therefore, it is desirable to provide systems and methods for stitching the images of the plurality of regions more precisely and efficiently.

SUMMARY

According to a first aspect of the present disclosure, a system is provided. The system may comprises at least one storage device including a set of instructions; and at least one processor configured to communicate with the at least one storage device, wherein when the set of instructions is executed by the processor, cause the at least one processor to perform operations. The operations may include obtaining a plurality of protocols for scanning a subject using a scanner, wherein the plurality of protocols correspond to a plurality of regions of the subject, respectively; determining one or more stitching parameters between protocols corresponding to each pair of neighboring regions of the plurality of regions; generating image stitching verification data associated with the plurality of regions based at least in part on at least one of the one or more stitching parameters between protocols corresponding to each pair of neighboring regions of the plurality of regions; and directing the scanner to scan the subject based at least in part on the image stitching verification data.

According to a second aspect of the present disclosure, a method implemented on a computing device having a processor and a computer-readable storage device is provided. The method may include obtaining a plurality of protocols for scanning a subject using a scanner, wherein the plurality of protocols correspond to a plurality of regions of the subject, respectively; determining one or more stitching parameters between protocols corresponding to each pair of neighboring regions of the plurality of regions; generating image stitching verification data associated with the plurality of regions based at least in part on at least one of the one or more stitching parameters between protocols corresponding to each pair of neighboring regions of the plurality of regions; and directing the scanner to scan the subject based at least in part on the image stitching verification data.

According to a third aspect of the present disclosure, a non-transitory computer-readable storage medium including instructions is provided. When the non-transitory computer-readable storage medium is accessed by at least one processor of a system, the system may be caused to perform a method. The method may include obtaining a plurality of protocols for scanning a subject using a scanner, wherein the plurality of protocols correspond to a plurality of regions of the subject, respectively; determining one or more stitching parameters between protocols corresponding to each pair of neighboring regions of the plurality of regions; generating image stitching verification data associated with the plurality of regions based at least in part on at least one of the one or more stitching parameters between protocols corresponding to each pair of neighboring regions of the plurality of regions; and directing the scanner to scan the subject based at least in part on the image stitching verification data.

In some embodiments, the image stitching verification data relates to at least one group of image stitching conditions, the generating image stitching verification data including determining whether the one or more stitching parameters between protocols corresponding to each pair of neighboring regions satisfy the at least one group of image stitching conditions.

In some embodiments, the directing the scanner to scan the subject based at least in part on the image stitching verification data includes directing the scanner to scan the plurality of regions of the subject according to the plurality of protocols, respectively, in response to determining that the one or more stitching parameters between protocols corresponding to each pair of neighboring regions satisfy the at least one group of image stitching conditions.

In some embodiments, the operations further includes obtaining scanning data of the plurality of regions of the subject generated by the scanner; reconstructing one or more images of each of the plurality of regions of the subject based on the scanning data; and generating an image of the subject by stitching, according to the one or more stitching parameters between protocols corresponding to each pair of neighboring regions, the one or more reconstructed images of each of the plurality of regions.

In some embodiments, the directing the scanner to scan the subject based at least in part on the image stitching verification data includes identifying a pair of neighboring regions in which an error exists in at least one of the one or more stitching parameters between protocols corresponding to the pair of neighboring regions; and generating a parameter adjustment recommendation for adjusting at least one of the one or more stitching parameters between protocols corresponding to the identified pair of neighboring regions, in response to determining that the at least one of the one or more stitching parameters between protocols corresponding to the identified pair of neighboring regions do not satisfy one or more of the at least one group of image stitching conditions.

In some embodiments, the determining whether the one or more stitching parameters between protocols corresponding to each pair of neighboring regions satisfy the at least one group of image stitching conditions includes at least one of determining whether imaging parameters of the plurality of regions are consistent, or determining whether spatial parameters corresponding to images of each pair of neighboring regions satisfy a spatial stitching condition.

In some embodiments, the determining whether the imaging parameters of the plurality of regions are consistent includes determining whether at least one of sequence types, weighting schemes, or distortion rectifications of the plurality of regions are consistent.

In some embodiments, the determining whether spatial parameters corresponding to images of each pair of neighboring regions satisfy a spatial stitching condition includes determining whether an image of a region is included in an image of another region among the plurality of regions, determining whether images of each pair of neighboring regions at least in part overlap, or determining whether an angle between images of each pair of neighboring regions satisfies an image angle condition.

In some embodiments, the operations further includes obtaining a parameter adjustment instruction from a user; and adjusting at least one of the one or more stitching parameters between protocols corresponding to at least one pair of neighboring regions according to the parameter adjustment instruction.

In some embodiments, the operations further includes obtaining a protocol modification instruction from a user; and modifying at least part of the plurality of protocols according to the protocol modification instruction.

In some embodiments, the modifying at least part of the plurality of protocol includes adding into or deleting from the plurality of protocols at least one protocol.

In some embodiments, the operations further includes determining one or more scanning parameters for each of the plurality of regions based on the plurality of protocols; and generating the image stitching verification data associated with the plurality of regions based further on at least one of the one or more scanning parameters for each of the plurality of regions.

According to a fourth aspect of the present disclosure, a system is provided. The system may comprises at least one storage device including a set of instructions; and at least one processor configured to communicate with the at least one storage device, wherein when the set of instructions is executed by the processor, cause the at least one processor to perform operations. The operations may include obtaining a plurality of protocols for scanning a subject using a scanner, wherein the plurality of protocols correspond to a plurality of regions of the subject, respectively; determining one or more scanning parameters for each of the plurality of regions based on the plurality of protocols; determining one or more stitching parameters between protocols corresponding to each pair of neighboring regions of the plurality of regions; generating image stitching verification data associated with the plurality of regions based on at least one of the one or more scanning parameters of each region and the one or more stitching parameters between protocols corresponding to each pair of neighboring regions of the plurality of regions; and directing the scanner to scan the subject based at least in part on the image stitching verification data.

According to a fifth aspect of the present disclosure, a method implemented on a computing device having a processor and a computer-readable storage device is provided. The method may include obtaining a plurality of protocols for scanning a subject using a scanner, wherein the plurality of protocols correspond to a plurality of regions of the subject, respectively; determining one or more scanning parameters for each of the plurality of regions based on the plurality of protocols; determining one or more stitching parameters between protocols corresponding to each pair of neighboring regions of the plurality of regions; generating image stitching verification data associated with the plurality of regions based on at least one of the one or more scanning parameters of each region and the one or more stitching parameters between protocols corresponding to each pair of neighboring regions of the plurality of regions; and directing the scanner to scan the subject based at least in part on the image stitching verification data.

According to a sixth aspect of the present disclosure, a non-transitory computer-readable storage medium including instructions is provided. When the non-transitory computer-readable storage medium is accessed by at least one processor of a system, the system may be caused to perform a method. The method may include obtaining a plurality of protocols for scanning a subject using a scanner, wherein the plurality of protocols correspond to a plurality of regions of the subject, respectively; determining one or more scanning parameters for each of the plurality of regions based on the plurality of protocols; determining one or more stitching parameters between protocols corresponding to each pair of neighboring regions of the plurality of regions; generating image stitching verification data associated with the plurality of regions based on at least one of the one or more scanning parameters of each region and the one or more stitching parameters between protocols corresponding to each pair of neighboring regions of the plurality of regions; and directing the scanner to scan the subject based at least in part on the image stitching verification data.

In some embodiments, the image stitching verification data relates to at least one group of image stitching conditions, the generating image stitching verification data including determining whether the one or more scanning parameters of each region and the one or more stitching parameters between protocols corresponding to each pair of neighboring regions satisfy the at least one group of image stitching conditions.

In some embodiments, the directing the scanner to scan the subject based at least in part on the image stitching verification data includes directing the scanner to scan the plurality of regions of the subject according to the plurality of protocols, respectively, in response to determining that the one or more scanning parameters of each region and the one or more stitching parameters between protocols corresponding to each pair of neighboring regions satisfy the at least one group of image stitching conditions.

In some embodiments, the operations further including obtaining scanning data of the plurality of regions of the subject generated by the scanner; reconstructing one or more images of each of the plurality of regions of the subject based on the scanning data; and generating an image of the subject by stitching, according to the one or more stitching parameters between protocols corresponding to each pair of neighboring regions, the one or more reconstructed images of each of the plurality of regions.

In some embodiments, the directing the scanner to scan the subject based at least in part on the image stitching verification data includes identifying a region in which an error exists in at least one of the one or more scanning parameters of the region or a pair of neighboring regions in which an error exists in at least one of the one or more stitching parameters between protocols corresponding to the pair of neighboring regions; and generating a parameter adjustment recommendation for adjusting at least one of the one or more scanning parameters of the identified region or at least one of the one or more stitching parameters between protocols corresponding to the identified pair of neighboring regions, in response to determining that the at least one of the one or more scanning parameters of the identified region or the at least one of the one or more stitching parameters between protocols corresponding to the identified pair of neighboring regions do not satisfy one or more of the at least one group of image stitching conditions.

In some embodiments, the determining whether the one or more scanning parameters of each region and the one or more stitching parameters between protocols corresponding to each pair of neighboring regions satisfy the at least one group of image stitching conditions includes at least one of determining whether images of each region satisfy a regional stitching condition, determining whether the imaging parameters of the plurality of regions are consistent, or determining whether spatial parameters corresponding to images of each pair of neighboring regions satisfy a spatial stitching condition.

In some embodiments, the determining whether an image corresponding to each region satisfies a regional stitching condition includes at least one of determining whether images of each of the plurality of regions are available according to the plurality of protocols, determining whether directions of the images of the plurality of regions are consistent, or determining whether at least one of the images of the plurality of regions is not an original image.

In some embodiments, the determining whether the imaging parameters of the plurality of regions are consistent includes determining whether at least one of sequence types, weighting schemes, or distortion rectifications of the plurality of regions are consistent.

In some embodiments, the determining whether spatial parameters corresponding to images of each pair of neighboring regions satisfy a spatial stitching condition includes determining whether an image of a region is included in an image of another region among the plurality of regions, determining whether images of each pair of neighboring regions at least in part overlap, or determining whether angles between images of each pair of neighboring regions satisfies an image angle condition.

In some embodiments, the operations further includes obtaining a parameter adjustment instruction from a user; and adjusting at least one of the one or more scanning parameters of at least one region or the one or more stitching parameters between protocols corresponding to at least one pair of neighboring regions according to the parameter adjustment instruction.

In some embodiments, the operations further includes obtaining a protocol modification instruction from a user; and adding into or deleting from the plurality of protocols at least one protocol according to the protocol modification instruction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 includes a flowchart illustrating an exemplary process for generating an image of a subject according to some embodiments of the present disclosure;

FIG. 8 includes a flowchart illustrating an exemplary process for generating an image of a subject according to some embodiments of the present disclosure;

FIG. 9 includes a flowchart illustrating an exemplary process for generating an image of a subject according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
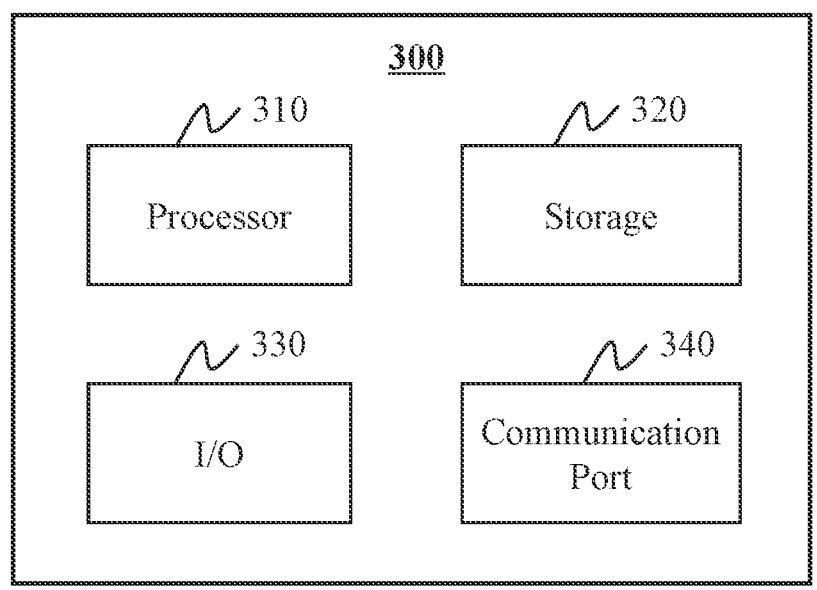
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive imaging, such as for disease diagnostic or research purposes. While the systems and methods disclosed in the present disclosure are described primarily regarding image stitching in an imaging system. It should be understood that this is only for illustration purposes. In some embodiments, the imaging system may include a single modality imaging system and/or a multi-modality imaging system. The single modality imaging system may include, for example, an MRI system, a PET system, a CT system, a SPECT system, an ultrasonic imaging system, an X-ray imaging system, etc. The multi-modality imaging system may include a combination of two or more of the imaging systems exemplified above. The following descriptions are provided, unless otherwise stated expressly, with reference to an MRI system for illustration purposes and not intended to be limiting.

An aspect of the present disclosure relates to imaging systems and methods involving image stitching. Before a scanner scans a subject, a plurality of protocols for scanning the subject may be obtained. The plurality of protocols may correspond to a plurality of regions of the subject, respectively. One or more scanning parameters for each of the plurality of regions may be determined based on the plurality of protocols. Besides, one or more stitching parameters between protocols corresponding to each pair of neighboring regions of the plurality of regions may be determined. A determination as to whether a stitched image of the subject can be generated may be made based on at least one of the one or more scanning parameters of each region and the one or more stitching parameters between protocols corresponding to each pair of neighboring regions. If it is determined that the stitched image of the subject can be generated, the scanner may be directed to scan the plurality of regions. In this case, a success rate of the image stitching may be improved, repetitive scans of the subject owing to errors in image stitching may be avoided, and the imaging process of the subject may be optimized, thereby shortening the time for imaging scan, and improving user experiences.

Figure 1:
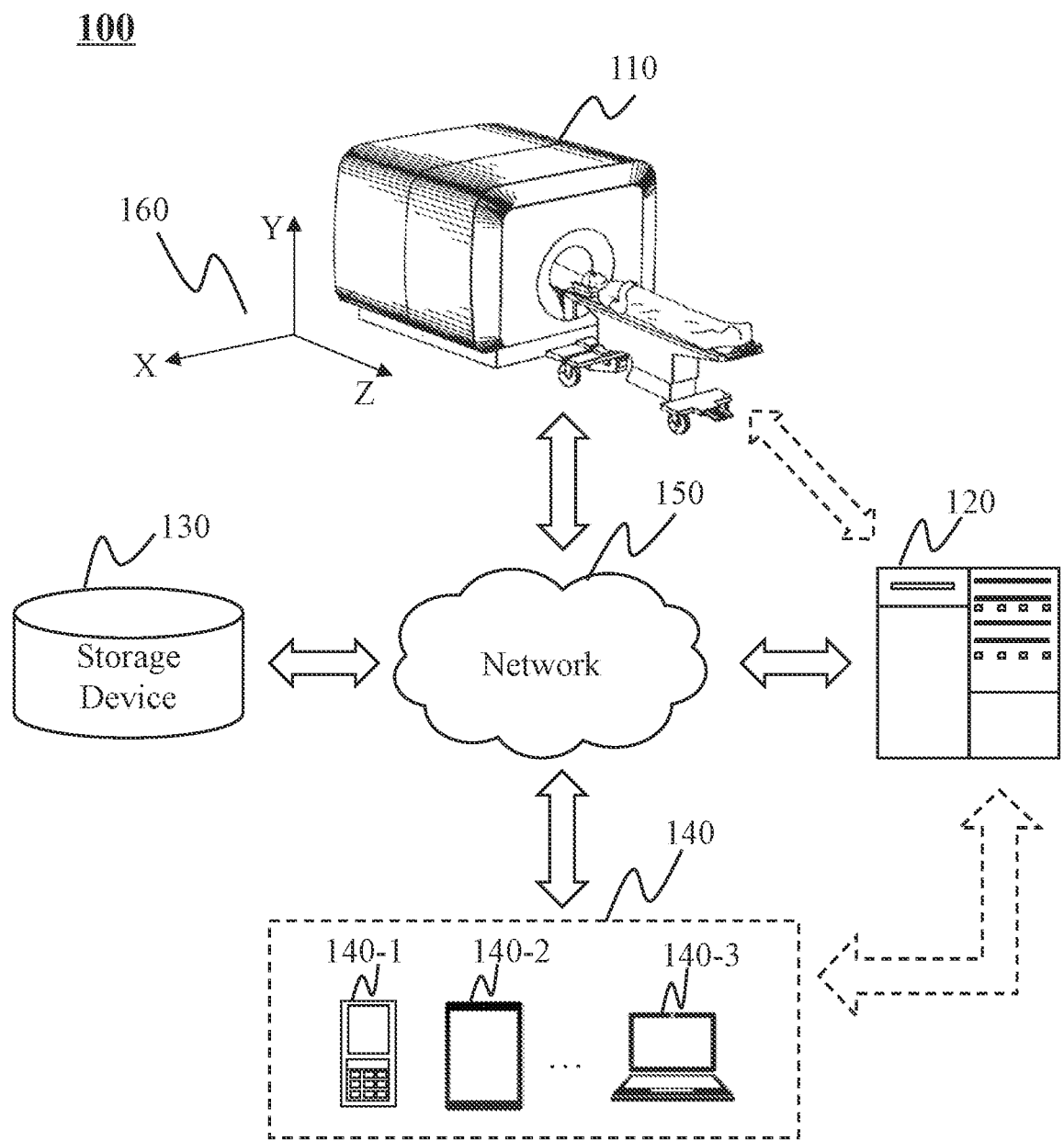
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown in FIG. 1, the imaging system 100 may include a scanner 110, a processing device 120, a storage device 130, one or more terminals 140, and a network 150. In some embodiments, the scanner 110, the processing device 120, the storage device 130, and/or the terminal(s) 140 may be connected to and/or communicate with each other via a wireless connection, a wired connection, or a combination thereof. The connections between the components in the imaging system 100 may be variable. For example, the scanner 110 may be connected to the processing device 120 through the network 150. As another example, the scanner 110 may be connected to the processing device 120 directly.

The scanner 110 may be configured to scan a subject to acquire image data, such as echo signals (or MR signals) associated with the subject. For example, the scanner 110 may scan the subject by executing a plurality of protocols. In some embodiments, the scanner 110 may include, for example, a main magnet, a gradient coil (or also referred to a spatial encoding coil), a radio frequency (RF) coil, etc., as described in connection with FIG. 2. In some embodiments, the scanner 110 may be a permanent magnet MR scanner, a superconducting electromagnet MR scanner, or a resistive electromagnet MR scanner, etc., according to types of the main magnet. In some embodiments, the scanner 110 may be a high-field MR scanner, a mid-field MR scanner, and a low-field MR scanner, etc., according to the intensity of the magnetic field.

The subject scanned by the scanner 110 may be biological or non-biological. For example, the subject may include a patient, a man-made object, etc. As another example, the subject may include a specific portion, organ, tissue, and/or a physical point of the patient. Merely by way of example, the subject may include the head, the brain, the neck, the body, shoulders, arms, the thorax, the cardiac, the stomach, blood vessels, soft tissue, knees, feet, or the like, or a combination thereof.

For illustration purposes, a coordinate system 160 including an X axis, a Y axis, and a Z axis is provided in FIG. 1. The X axis and the Z axis shown in FIG. 1 may be horizontal, and the Y-axis may be vertical. As illustrated, the positive X direction along the X axis may be from the right side to the left side of the scanner 110 seen from the direction facing the front of the scanner 110; the positive Y direction along the Y axis shown in FIG. 1 may be from the lower part to the upper part of the scanner 110; the positive Z direction along the Z axis shown in FIG. 1 may refer to a direction in which the subject is moved out of the scanning channel (or referred to as the bore) of the scanner 110.

In some embodiments, the scanner 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the scanner 110 may be found elsewhere in the present disclosure. See, e.g., FIG. 2 and the description thereof.

The processing device 120 may process data and/or information obtained from the scanner 110, the storage device 130, and/or the terminal(s) 140. For example, the processing device 120 may obtain a plurality of protocols for scanning the subject, and determine one or more scanning parameters of the scanner 110 based on the plurality of protocols. As another example, the processing device 120 may obtain echo signals from the scanner 110, and reconstruct one or more images of the subject based on the echo signals. In some embodiments, the processing device 120 may be a single server or a server group. The server group may be centralized or distributed. In some embodiments, the processing device 120 may be local or remote. For example, the processing device 120 may access information and/or data from the scanner 110, the storage device 130, and/or the terminal(s) 140 via the network 150. As another example, the processing device 120 may be directly connected to the scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the scanner 110, the processing device 120, the terminal(s) 140, etc. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the imaging system 100 (e.g., the scanner 110, the processing device 120, and/or the terminal(s) 140). One or more components of the imaging system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the imaging system 100. For example, the terminal(s) 140 may receive an instruction to cause the scanner 110 to scan the subject from the user. As another example, the terminal(s) 140 may receive a processing result (e.g., one or more images of the subject) from the processing device 120 and display the processing result to the user. In some embodiments, the terminal(s) 140 may be connected to and/or communicate with the scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the scanner 110.

The network 150 may include any suitable network that can facilitate the exchange of information and/or data for the imaging system 100. In some embodiments, one or more components of the imaging system 100 (e.g., the scanner 110, the processing device 120, the storage device 130, the terminal(s) 140, etc.) may communicate information and/or data with one or more other components of the imaging system 100 via the network 150. For example, the processing device 120 may obtain a plurality of protocols from the storage device 130 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the imaging system 100 may include one or more additional components and/or one or more components described above may be omitted. Additionally or alternatively, two or more components of the imaging system 100 may be integrated into a single component. For example, the processing device 120 may be integrated into the scanner 110. As another example, a component of the imaging system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
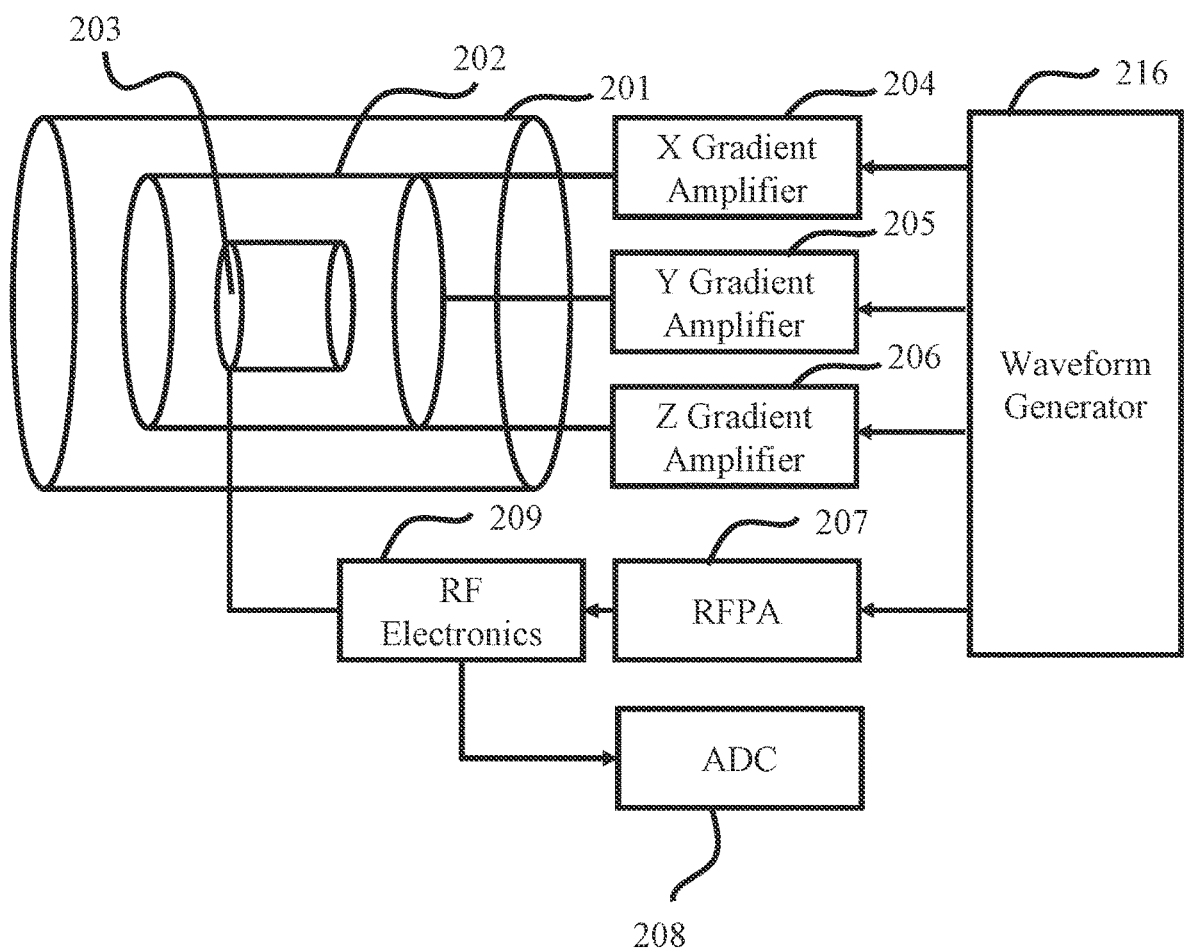
FIG. 2 is a schematic diagram illustrating an exemplary MR scanner according to some embodiments of the present disclosure.

FIG. 2 is a schematic diagram illustrating an exemplary scanner 110 according to some embodiments of the present disclosure. One or more components of the scanner 110 are illustrated in FIG. 2. As illustrated, a main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore within which the subject is placed. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MR scanner or an open-bore MR scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the scanner 110 may further include a subject positioning system (not shown). The subject positioning system may include a subject cradle and a transport device. The subject may be placed on the subject cradle and be positioned by the transport device within the bore of the main magnet 201.

MRI systems (e.g., the imaging system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase may be superimposed on the uniform magnetic field such that the RF excitation signal excites the H atoms in a desired slice of the patient's body, and unique phase and frequency information are encoded in the echo signal depending on the location of the H atoms in the "image slice."

Typically, one or more portions of the patient's body to be imaged are scanned by a sequence of measurement cycles in which the RF excitation signals and the magnetic field gradients Gx, Gy, and Gz vary according to an MRI imaging protocol that is being used. A protocol may be designed for each of the one or more portions of the patient's body to be imaged. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct one or more images in accordance with the protocols that are used.

FIG. 3 is a schematic diagram illustrating exemplary hardware and/or software components of a computing device 300 according to some embodiments of the present disclosure. The computing device 300 may be used to implement any component of the imaging system 100 as described herein. For example, the processing device 120 and/or the terminal 140 may be implemented on the computing device 300, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process data obtained from the scanner 110, the terminal(s) 140, the storage device 130, and/or any other component of the imaging system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the scanner 110, the terminal(s) 140, the storage device 130, and/or any other component of the imaging system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to execute for determining whether an overall image of the subject can be generated by stitching images of a plurality of regions of the subject.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 150) to facilitate data communications. The communication port 340 may establish connections between the processing device 120 and the scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
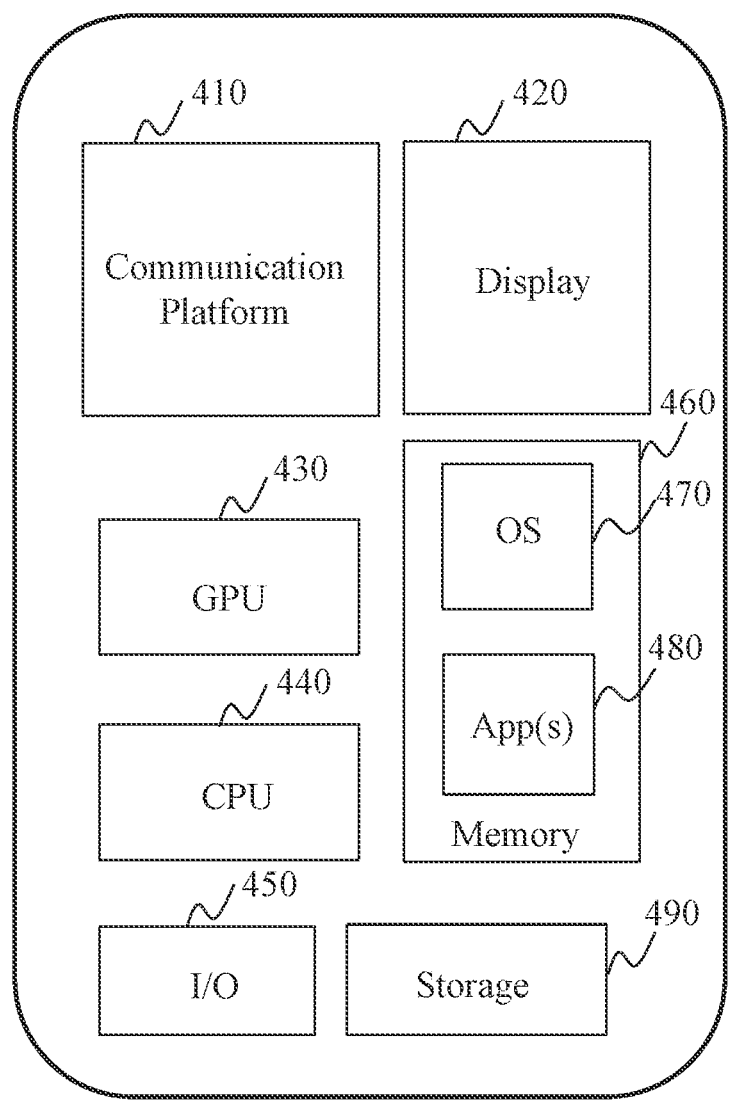
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 140 and/or the processing device 120) of the imaging system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™ Windows Phone™) and one or more applications 480 may be loaded into the memory 460 from the storage 490 in order to be executed by the CPU 440. The applications 480 may include a browser or any other suitable mobile apps for receiving and rendering information relating to the imaging system 100. User interactions with the information stream may be achieved via the I/O 450 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
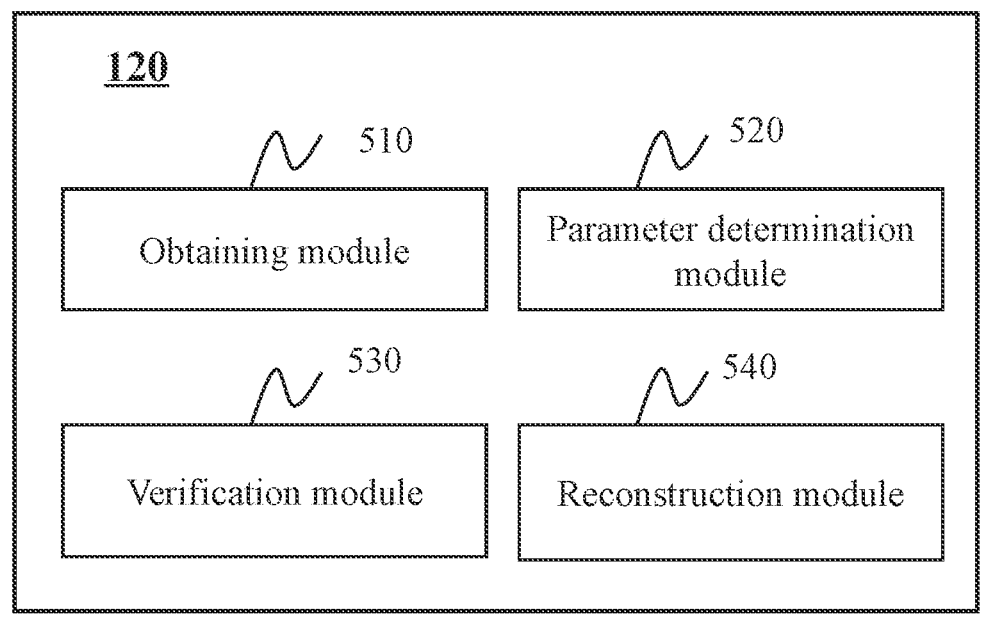
FIG. 5 is a block diagram illustrating an exemplary processing device according to some embodiments of the present disclosure.

FIG. 5 is a block diagram illustrating an exemplary processing device 120 according to some embodiments of the present disclosure. As shown in FIG. 5, the processing device 120 may include an obtaining module 510, a parameter determination module 520, a verification module 530, and a reconstruction module 540. The connection(s) between the modules may be wireless or wired.

The obtaining module 510 may obtain data and/or information. The obtaining module 510 may obtain data and/or information from the scanner 110, the processing device 120, the storage device 130, the terminal(s) 140, or any devices or components capable of storing data via the network 150. For example, the obtaining module 510 may obtain data and/or information from a medical cloud data center (not shown) via the network 150. The obtained data and/or information may include a protocol corresponding to a region of a subject, data of the subject (e.g., the height, the weight, the age, etc.), algorithms, parameters (e.g., one or more stitching parameters between protocols corresponding to each pair of neighboring regions of the plurality of regions), program codes, information of a subject, or the like, or a combination thereof. In some embodiments, the obtaining module 510 may obtain a plurality of protocols for scanning the subject using a scanner.

Each of the plurality of protocols may include a certain number of pulse sequences oriented in different planes and/or with different parameters. The protocol may also include information regarding image contrast and/or ratio, an ROI, slice thickness, a weighting scheme (e.g., T1 weighted, T2 weighted, proton density weighted, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a count or number of images, direction of the images, or the like, or any combination thereof. The plurality of protocols may be obtained from a storage device (e.g., the storage device 130, the storage 320, the storage 490, cloud storage, etc.).

The parameter determination module 520 may determine one or more scanning parameters for each of the plurality of regions and/or one or more stitching parameters between protocols corresponding to each pair of neighboring regions of the plurality of regions. In some embodiments, the parameter determination module 520 may obtain the plurality of protocols from the obtaining module 510. The parameter determination module 520 may determine the one or more scanning parameters for each of the plurality of regions and/or one or more stitching parameters between protocols corresponding to each pair of neighboring regions of the plurality of regions based on the plurality of protocols.

The one or more scanning parameters for each of the plurality of regions may refer to parameters related to the imaging process of each of the plurality of regions. Exemplary scanning parameters for each of the plurality of regions may relate to spatial information, pulse sequences, weighting schemes, and/or distortion rectifications of the region.

The one or more stitching parameters between protocols corresponding to each pair of neighboring regions of the plurality of regions may refer to parameters for stitching images of each pair of neighboring regions of the plurality of regions. Exemplary stitching parameters may include a positional relationship of each pair of neighboring regions, stitching algorithms, rectification algorithms, relative positions of images corresponding to each pair of neighboring regions of the plurality of regions, etc.

The verification module 530 may generate image stitching verification data associated with the plurality of regions. In some embodiments, the verification module 530 may obtain the one or more scanning parameters of each region and the one or more stitching parameters between protocols corresponding to each pair of neighboring regions of the plurality of regions from the parameter determination module 520. The verification module 530 may generate the image stitching verification data associated with the plurality of regions based on at least one of the one or more scanning parameters of each region and the one or more stitching parameters between protocols corresponding to each pair of neighboring regions of the plurality of regions.

The image stitching verification data may include data indicating the feasibility of generating a stitched image of the subject (i.e., whether a stitched image of the subject can be generated by stitching images of the plurality of regions). In some embodiments, the image stitching verification data may relate to at least one group of image stitching conditions.

In some embodiments, the image stitching verification data may be generated by determining whether images of each region satisfy a regional stitching condition, whether imaging parameters of the plurality of regions are consistent, and/or whether spatial parameters corresponding to images of each pair of neighboring regions satisfy a spatial stitching condition. The determinations or at least a part thereof may constitute the at least one group of image stitching conditions. In some embodiments, the determination as to whether images of each region satisfy a regional stitching condition may be made based on the one or more scanning parameters of each of the plurality of regions. The determination as to whether the imaging parameters of the plurality of regions are consistent may be made based on the parameters to be verified. The determination as to whether spatial parameters corresponding to images of each pair of neighboring regions satisfy a spatial stitching condition may also be made based on the parameters to be verified.

The reconstruction module 540 may reconstruct an image of a region. In some embodiments, if the image stitching verification data indicates that the parameters to be verified satisfy the at least one group of image stitching conditions (i.e., the image stitching may succeed), the scanner 110 may be directed to scan the plurality of regions according to the plurality of protocols, respectively. After the plurality of regions of the subject are scanned, scanning data of the plurality of regions generated by the scanner may be obtained. The reconstruction module 540 may reconstruct images of each of the plurality of regions of the subject based on the scanning data. A stitched image of the entire subject may be generated by stitching, according to the one or more stitching parameters between protocols corresponding to each pair of neighboring regions, the reconstructed images of the plurality of regions.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may include one or more additional modules, such as a storage module (not shown) for storing data, an instruction generation module for generating instructions to direct a scanner to scan the subject based at least in part on the image stitching verification data. As another example, one or more modules of the processing device 120 described above may be omitted. Additionally or alternatively, two or more modules of the processing device 120 may be integrated into a single component. A module of the processing device 120 may be divided into two or more units.

FIG. 6 includes a flowchart illustrating an exemplary process for generating an image of a subject according to some embodiments of the present disclosure. In some embodiments, the process 600 may be executed by the imaging system 100. For example, the process 600 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 600.

In 610, a plurality of protocols for scanning a subject using a scanner may be obtained, the plurality of protocols corresponding to a plurality of regions of the subject, respectively. In some embodiments, the plurality of protocols may be obtained by the obtaining module 510.

The subject may be a patient, an animal, a man-made object (e.g., a phantom), etc. In some embodiments, the subject may include a specific portion of a body, such as the head, the thorax, the abdomen, or the like, or a combination thereof, of a patient. In some embodiments, the subject may include a specific organ, such as the heart, the esophagus, the trachea, the bronchus, the stomach, the gallbladder, the small intestine, the colon, the bladder, the ureter, the uterus, the fallopian tube, etc., or a portion thereof, of a patient.

The scanner may include an MR scanner, a PET scanner, a CT scanner, a SPECT scanner, an ultrasonic scanner, an X-ray scanner, a PET-CT scanner, a PET-MR scanner, or the like, or any combination thereof. Merely for illustration purposes, the following descriptions in FIGS. 6 through 10 are provided with reference to an MR scanner unless otherwise stated expressly, which is not intended to be limiting.

The scanner may have a field of view (FOV) of a particular size. If the size of the subject exceeds the particular size of the FOV of the scanner, the scanning of the subject may be performed in a plurality of sessions corresponding to a plurality of regions of the subject according to, for example, a scanning plan. Merely by way of example, the scanning of a patient may be scheduled to be performed in five sessions corresponding to five regions of the subject before the scanner starts to scan the entire body of the patient. The five regions may correspond to the head, the neck, the thorax, the abdomen, and the lower limbs of the patient, respectively.

During the scanning process of the subject, the plurality of regions of the subject may be positioned in the FOV of the scanner sequentially. The positioning may be achieved by moving the subject (or a portion thereof) or moving the scanner (or a portion thereof) so that the region of the subject is positioned within the FOV of the scanner. In some embodiments, the plurality of regions of the subject may be positioned in the FOV of the scanner by adjusting a position of a couch supporting the subject. In some embodiments, each region of the subject may correspond to a certain position of the couch. A scan may be performed in a session on each of the plurality of regions according to a protocol corresponding to the region.

A protocol may be designed for each of the plurality of regions. A protocol may include a certain number of pulse sequences oriented in different planes and/or with different parameters. The protocol may also include information regarding image contrast and/or ratio, an ROI, slice thickness, a weighting scheme (e.g., T1 weighted, T2 weighted, proton density weighted, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a count or number of images, direction of the images, or the like, or any combination thereof.

The plurality of protocols may be obtained from a storage device (e.g., the storage device 130, the storage 320, the storage 490, a cloud storage, etc.). For example, the obtaining module 510 may retrieve the plurality of protocols from a database including protocols of various parameters stored in the storage device. The plurality of protocols may be retrieved from the database according to an instruction of a user (e.g., a doctor, a technician, etc.), default settings of the imaging system 100, etc.

In 620, one or more scanning parameters for each of the plurality of regions may be determined based on the plurality of protocols, and one or more stitching parameters between protocols corresponding to each pair of neighboring regions of the plurality of regions may be determined. In some embodiments, the one or more scanning parameters for each of the plurality of regions and the one or more stitching parameters between protocols corresponding to each pair of neighboring regions of the plurality of regions may also be referred to as "parameters to be verified" for brevity. In some embodiments, the parameters to be verified may be determined by the parameter determination module 520.

The one or more scanning parameters for each of the plurality of regions may refer to parameters related to the imaging process of each of the plurality of regions. Exemplary scanning parameters for each of the plurality of regions may relate to spatial information, pulse sequences, weighting schemes, and/or distortion rectifications of the region. Spatial information of a region may include, for example, counts, directions, positions, sizes, resolutions, etc., of images corresponding to the region. Exemplary pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. Exemplary weighting schemes of the region may include T1 weighted, T2 weighted, proton density weighted, etc. The distortion rectifications for a region may refer to manners in which geometric distortions in image are corrected. The distortion rectifications may include two-dimensional (2D) rectification, three-dimensional (3D) rectification, etc. In some embodiments, the one or more scanning parameters for each of the plurality of regions may be included in the protocol corresponding to the region. In some embodiments, the one or more scanning parameters for each of the plurality of regions may be resolved from the protocol corresponding to the region.

The one or more stitching parameters between protocols corresponding to each pair of neighboring regions of the plurality of regions may refer to parameters for stitching images of each pair of neighboring regions of the plurality of regions. Exemplary stitching parameters may include a positional relationship of each pair of neighboring regions, stitching algorithms, rectification algorithms, relative positions of images corresponding to each pair of neighboring regions of the plurality of regions, etc. The positional relationship of each pair of neighboring regions may include an inclusion relationship, a completely overlapping relationship, a partially overlapping relationship, an abutting relationship, and/or a noncontiguous relationship.

Take a pair of neighboring regions A and B as an example. If the region A is completely within the region B, the positional relationship of the pair of neighboring regions A and B may be deemed the inclusion relationship. For the pair of neighboring regions A and B that are of the inclusion relationship, at least a portion of the boundary of the region A is enclosed within the boundary of the region of region B. In some embodiments, for the pair of neighboring regions A and B that are of the inclusion relationship, a portion of the boundary of the region A may coincide with a portion of the boundary of the region B. If the region A and the region B completely overlap, the positional relationship of the pair of neighboring regions A and B may be deemed the completely overlapping relationship. For the pair of neighboring regions A and B that are of the completely overlapping relationship, the entire boundary of the region A coincides with the entire boundary of the region B. If the region A and the region B partially overlap, the positional relationship of the pair of neighboring regions A and B may be deemed the partially overlapping relationship. For the pair of neighboring regions A and B that are of the partially overlapping relationship, a portion of the region A is located within the region B, and a portion of the region A is located outside the region B; a portion of the boundary of the region A is enclosed within the boundary of the region B, while a portion of the boundary of the region A is located outside the boundary of the region B. If the region A abuts against the region B, the positional relationship of the pair of neighboring regions A and B may be the abutting relationship. For the pair of neighboring regions A and B that are of the abutting relationship, the region A is located completely outside the region B; a portion of the boundary of the region A coincides with a portion of the boundary of the region B, while a portion of the boundary of the region A is located outside the boundary of the region B. If the region A is spaced apart from the region B, the positional relationship of the pair of neighboring regions A and B may be deemed the noncontiguous relationship.

Exemplary stitching algorithms may include a Harris algorithm, a small univalue segment assimilating nucleus (SUSAN) algorithm, a scale-invariant feature transform (SIFT) algorithm, a speeded-up robust feature (SURF) algorithm, etc. Exemplary rectification algorithms may include a linearity transform, a quadratic polynomial transform, a neural network algorithm, a grey level transform, a histogram transform, etc.

In some embodiments, the one or more stitching parameters between protocols corresponding to each pair of neighboring regions of the plurality of regions may be set by a user (e.g., a doctor, a technician, etc.), according to default settings of the imaging system, etc. In some embodiments, the one or more stitching parameters between protocols corresponding to each pair of neighboring regions may also be included in the plurality of protocols. The one or more stitching parameters between protocols corresponding to each pair of neighboring regions of the plurality of regions may be derived from the protocols corresponding to the plurality of regions.

In 630, image stitching verification data associated with the plurality of regions may be generated based on at least one of the one or more scanning parameters of each region and the one or more stitching parameters between protocols corresponding to each pair of neighboring regions of the plurality of regions. In some embodiments, the image stitching verification data may be generated by the verification module 530.

The image stitching verification data may include data indicating the feasibility of generating a stitched image of the subject (i.e., whether a stitched image of the subject can be generated by stitching images of the plurality of regions). In some embodiments, the image stitching verification data may relate to at least one group of image stitching conditions. In some embodiments, the image stitching verification data may be generated by determining whether the parameters to be verified satisfy the at least one group of image stitching conditions.

In some embodiments, attributes (e.g., whether one or more images of each of the plurality of regions are available, directions, whether one or more images of each of the plurality of regions are original images, etc.) of images of each of the plurality of regions may be determined based on the one or more scanning parameters of each of the plurality of regions. The image stitching verification data may be generated based on the attributes of the images of each of the plurality of regions and the one or more stitching parameters between protocols corresponding to each pair of neighboring regions. In some embodiments, the attributes of the images of each of the plurality of regions may be verified (e.g., according to the at least one group of image stitching conditions) under the premise of the one or more stitching parameters between protocols corresponding to each pair of neighboring regions of the plurality of regions.

In some embodiments, the image stitching verification data may be generated by determining whether images of each region satisfy a regional stitching condition, whether imaging parameters of the plurality of regions are consistent, and/or whether spatial parameters corresponding to images of each pair of neighboring regions satisfy a spatial stitching condition. The determinations or at least a part thereof may constitute the at least one group of image stitching conditions. In some embodiments, the determination as to whether images of each region satisfy a regional stitching condition may be made based on the one or more scanning parameters of each of the plurality of regions. The determination as to whether the imaging parameters of the plurality of regions are consistent may be made based on the parameters to be verified. The determination as to whether spatial parameters corresponding to images of each pair of neighboring regions satisfy a spatial stitching condition may also be made based on the parameters to be verified. It should be noted that the order in which the determinations are made and/or the content of the determinations are not limited to what is expressly exemplified in the present disclosure. In some embodiments, the content of the determinations may be adjusted according to the actual needs. For example, the content of the determinations may vary if the scanner is a CT scanner, a PET scanner, a PET-CT scanner, or a PET-MR scanner.

The regional stitching condition may relate to each of the plurality of regions. In some embodiments, the regional stitching condition corresponding to a region may relate to the suitability of one or more images of the region for image stitching (i.e., whether one or more images of a region are suitable for image stitching). If images corresponding to a region satisfy a regional stitching condition, it may indicate that the images of the region are suitable for image stitching. In some embodiments, the regional stitching condition may be associated with, for example, availability of at least one image of each region, consistency of the direction(s) of at least one image of each region, original image(s) of the region available, etc.

The imaging parameters for imaging a region of the subject may be associated with, for example, sequence types, weighting schemes, distortion rectifications, etc.

The spatial stitching condition may relate to each pair of neighboring regions of the plurality of regions. In some embodiments, the regional stitching condition corresponding to a pair neighboring regions may relate to an inclusion relationship, a partially overlapping relationship, an image angle condition, etc.

More details regarding the generation of the image stitching verification data may be found elsewhere in the present disclosure. See, for example, FIG. 7 and the descriptions thereof.

In 640, the scanner may be directed to scan the subject based at least in part on the image stitching verification data.

In some embodiments, the image stitching verification data may be output to a user (e.g., a doctor, a technician, etc.). For example, the image stitching verification data may be displayed on a display interface of a terminal device (e.g., a desktop, a laptop, the mobile device 400, etc.). In some embodiments, if the image stitching verification data indicates that the parameters to be verified satisfy the at least one group of image stitching conditions (i.e., the image stitching may succeed), the scanner 110 may be directed to scan the plurality of regions according to the plurality of protocols, respectively. After the plurality of regions of the subject are scanned, scanning data of the plurality of regions generated by the scanner may be obtained. Images of each of the plurality of regions of the subject may be reconstructed based on the scanning data. A stitched image of the entire subject may be generated by stitching, according to the one or more stitching parameters between protocols corresponding to each pair of neighboring regions, the reconstructed images of the plurality of regions.

In some embodiments, if the image stitching verification data indicates that at least one of the one or more scanning parameters of the identified region or at least one of the one or more stitching parameters between protocols corresponding to the identified pair of neighboring regions does not satisfy one or more of the at least one group of image stitching conditions (i.e., the image stitching may fail), the imaging system 100 may identify a region in which an error exists in at least one of the one or more scanning parameters of the region, or a pair of neighboring regions in which an error exists in at least one of the one or more stitching parameters between protocols corresponding to the pair of neighboring regions. The imaging system 100 may generate a parameter adjustment recommendation for adjusting the at least one of the one or more scanning parameters of the identified region or the at least one of the one or more stitching parameters between protocols corresponding to the identified pair of neighboring regions. As used herein, the errors may refer to inappropriateness of at least one of the parameters to be verified in terms of generating a stitched image of the entire subject. In some embodiments, the information output may include information relating to the identified region, the identified pair of neighboring regions, the error existed in the at least one of the one or more scanning parameters of the region, the error existed in the at least one of the one or more stitching parameters between protocols corresponding to the pair of neighboring regions, and/or the parameter adjustment recommendation through, e.g., the display interface of the terminal device.

According to the embodiments in the process 600, the operations 610 through 640 may be performed before the scanner 110 scans the subject. In this way, the feasibility of the generation of a stitched image of the subject may be verified in advance, the user may optimize at least one of the parameters to be verified according to the parameter adjustment recommendation if the generation of the image of the subject is infeasible, thereby improving the success rate of the image stitching, avoiding repetitive scanning of the subject, and reducing the time of the imaging scan.

Figure 7:
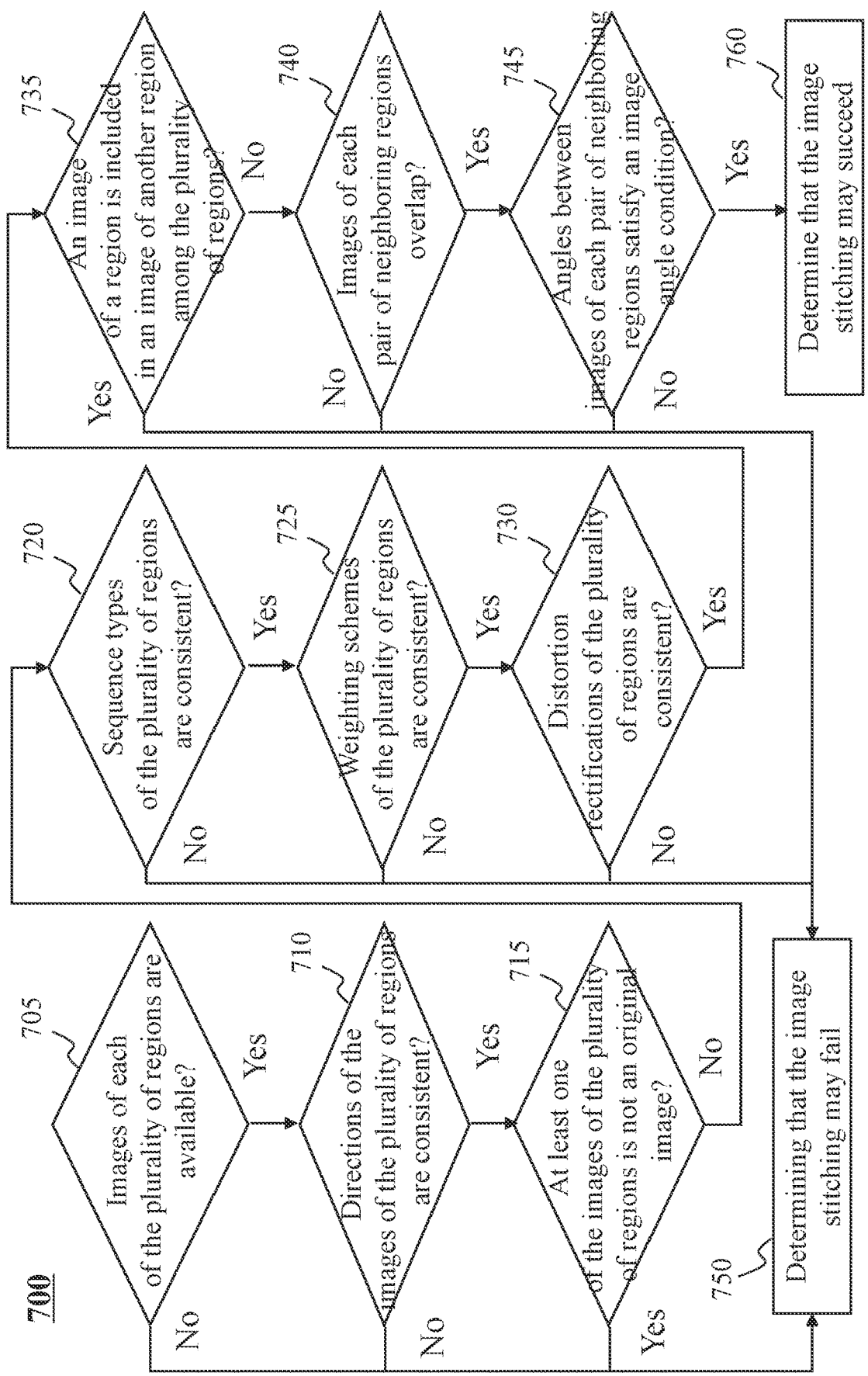
FIG. 7 includes a flowchart illustrating an exemplary process for generating image stitching verification data associated with a plurality of regions according to some embodiments of the present disclosure.

FIG. 7 includes a flowchart illustrating an exemplary process for generating image stitching verification data associated with a plurality of regions according to some embodiments of the present disclosure. In some embodiments, the process 700 may be executed by the imaging system 100. For example, the process 700 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 700. In some embodiments, the operation 630 of the process 600 may be performed according to the process 700.

To generate the image stitching verification data associated with the plurality of regions, determinations may be made as to one or more of whether images of each region satisfy a regional stitching condition corresponding to the region, whether imaging parameters of the plurality of regions are consistent, or whether spatial parameters corresponding to images of each pair of neighboring regions satisfy a spatial stitching condition. The image stitching verification data may be generated based on the determination(s). The order in which the determinations are made is not limited to what is expressly exemplified in the present disclosure. For example, the processing device (e.g., the verification module 530) may determine first whether images of each region satisfy a regional stitching condition corresponding to the region, then whether spatial parameters corresponding to images of each pair of neighboring regions satisfy a spatial stitching condition, and next whether imaging parameters of the plurality of regions are consistent sequentially. As another example, the processing device (e.g., the verification module 530) may determine first whether imaging parameters of the plurality of regions are consistent, then whether spatial parameters corresponding to images of each pair of neighboring regions satisfy a spatial stitching condition, and next whether images of each region satisfy a regional stitching condition corresponding to the region sequentially. As a further example, the processing device (e.g., the verification module 530) may determine whether images of each region satisfy a regional stitching condition corresponding to the region, whether imaging parameters of the plurality of regions are consistent, and whether spatial parameters corresponding to images of each pair of neighboring regions satisfy a spatial stitching condition simultaneously.

Merely for illustration purposes, the processing device (e.g., the verification module 530) may determine whether images of each region satisfy a regional stitching condition corresponding to the region in 705 through 715. The processing device (e.g., the verification module 530) may determine whether imaging parameters of the plurality of regions are consistent in 720 through 730. The processing device (e.g., the verification module 530) may determine whether spatial parameters corresponding to images of each pair of neighboring regions satisfy a spatial stitching condition in 735 through 745. The determinations in 705 through 745 or at least a part thereof may constitute the at least one group of image stitching conditions.

In 705, a determination as to whether one or more images of each of the plurality of regions are available may be made. In some embodiments, the one or more images of a region being available may indicate that the images of the region can be reconstructed if an MR scan is performed on the region according to the protocol corresponding to the region. For example, if the number or count of sampled points in a region are insufficient (e.g., smaller than a threshold), it may be determined that images of the region are unavailable. In some embodiments, images of a region being available may indicate that the quality of the images of the region satisfy a preset standard. For example, if values of noise in one or more images of the region are higher than a preset noise standard, it may be determined that images of the region are unavailable.

If images of the plurality of regions are available, the process may proceed to 710. If images of any one of the plurality of regions are unavailable, the process may proceed to 750.

In 710, a determination as to whether directions of the images of the plurality of regions are consistent may be made. A region of a subject may include one or more slices. The one or more slices may correspond to one or more images of the region, respectively. A direction of an image may be a direction of a normal vector perpendicular to a corresponding slice. In some embodiments, if directions of the images of plurality of regions are within a first range of a reference direction, it may be determined that the directions of the images of the plurality of regions are consistent. The reference direction may be any suitable direction, for example, the X direction, the Y direction, or the Z direction as illustrated in FIG. 1. The first range may be set by a user, according to default settings of the imaging system 100, etc. For example, the first range may be 5 degrees, 8 degrees, 10 degrees, etc.

If directions of the images of the plurality of regions are consistent, the process may proceed to 715. If directions of the images of the plurality of regions are inconsistent, the process may proceed to 750.

In 715, a determination as to whether at least one of the images of the plurality of regions is not an original image may be made. An original image may refer to an image reconstructed based on scanning data without being processed. If an original image of a region is processed, for example, in a particular manner or according to a particular algorithm, the processed image can not be used in the image stitching.

If the images of the plurality of regions are original images, the process may proceed to 720. If any one of images of a region is not an original image, the process may proceed to 750.

In 720, a determination as to whether sequence types of the plurality of regions are consistent may be made. Exemplary sequence types may include spin echo sequences, gradient echo sequences, diffusion sequences, inversion recovery sequences, or the like. The spin echo sequences may further include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like. The gradient echo sequences may further include a balanced steady-state free precession (bSSFP) pulse sequence, a spoiled gradient echo (GRE) pulse sequence, and an echo planar imaging (EPI) pulse sequence, a steady state free precession (SSFP), or the like. If the sequence types of the plurality of regions belong to a same type (e.g., FSE pulse sequence), it may be determined that the sequence types of the plurality of regions are consistent.

If the sequence types of the plurality of regions are consistent, the process may proceed to 725. If the sequence types of the plurality of regions are inconsistent, the process may proceed to 750.

In 725, a determination as to whether weighting schemes of the plurality of regions are consistent may be made. Exemplary weighting schemes may include T1 weighted, T2 weighted, proton density weighted, etc. If the weighting schemes of the plurality of regions belong to a same type (e.g., T1 weighted), it may be determined that the weighting schemes of the plurality of regions are consistent.

If the imaging types of the plurality of regions are consistent, the process may proceed to 730. If the imaging types of the plurality of regions are inconsistent the process may proceed to 750.

In 730, a determination as to whether distortion rectifications of the plurality of regions are consistent may be made. Exemplary distortion rectifications may include 2D rectification, 3D rectification, etc. If the distortion rectifications of the plurality of regions belong to a same type (e.g., 2D rectification), it may be determined that the distortion rectifications of the plurality of regions are consistent.

If the distortion rectifications of the plurality of regions are consistent, the process may proceed to 735. If the distortion rectifications of the plurality of regions are inconsistent, the process may proceed to 750.

In 735, a determination as to whether an image of a region is included in an image of another region among the plurality of regions may be made. In some embodiments, the determination as to whether an image of a region is included in an image of another region among the plurality of regions may be made based on the parameters to be verified. For example, if a rectangle scanning range of a region is included in a rectangle scanning range of another region, it may be determined that an image of the region is included in the image of the another region. The rectangle scanning range of a region may be expressed in the form of coordinates of four vertices of the rectangle.

If no image is included in another image, the process may proceed to 740. If an image of a region is included in an image of another region among the plurality of regions, the process may proceed to 750.

In 740, a determination as whether images of each pair of neighboring regions overlap may be made. In some embodiments, the determination as to whether images of each pair of neighboring regions partially overlap may also be made based on the parameters to be verified. For example, if a rectangle scanning range of a region and a rectangle scanning range of a neighboring region partially overlap, it may be determined that an image of the region and an image of the neighboring region partially overlap.

If the images of each pair of neighboring regions partially overlap, the process may proceed to 745. If images of at least one pair of neighboring regions do not overlap, the process may proceed to 750.

In 745, a determination as whether angle(s) between images of each pair of neighboring regions satisfy an image angle condition may be made.

The images of each pair of neighboring regions to be stitched may be substantially in parallel. The image angle condition may relate to a second range. Specifically, the image angle condition may be that angles of planes corresponding to the images of each pair of neighboring regions may need to be within the second range. The second range may be set by a user, according to default settings of the imaging system 100, etc. For example, the second range may be 1 degrees, 2 degrees, 5 degrees, 10 degrees, etc.

If the angles between images of each pair of neighboring regions satisfy the image angle condition, the process may proceed to 760. If an angle between images of at least one pair of neighboring regions does not satisfy the image angle condition, the process may proceed to 750.

In 750, the processing device 120 (e.g., the verification module 530) may determine that the image stitching may fail. In other words, an image of the subject can not be generated since the parameters to be verified do not satisfy the at least one group of image stitching conditions. Accordingly, the image stitching verification data indicating that the image stitching may fail may be generated.

In 760, the processing device 120 (e.g., the verification module 530) may determine that the image stitching may succeed. In other words, the image of the subject can be generated since the parameters to be verified satisfy the at least one group of image stitching conditions. Accordingly, the image stitching verification data indicating that the image stitching may succeed may be generated.

FIG. 8 includes a flowchart illustrating an exemplary process for generating an image of a subject according to some embodiments of the present disclosure. In some embodiments, the process 800 may be executed by the imaging system 100. For example, the process 800 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 800.

In 810, a plurality of protocols for scanning a subject using a scanner may be obtained, the plurality of protocols corresponding to a plurality of regions of the subject, respectively. In some embodiments, the plurality of protocols may be obtained from a storage device (e.g., the storage device 130, the storage 320, the storage 490, a cloud storage, etc.). For example, the obtaining module 510 may retrieve the plurality of protocols from a database including protocols of various parameters stored in the storage device. The plurality of protocols may be retrieved from the database according to an instruction of a user (e.g., a doctor, a technician, etc.), default settings of the imaging system 100, etc. In some embodiments, the operation 810 may be similar to or the same as the operation 610 of the process 600 as illustrated in FIG. 6, the description of which is not repeated here.

In 820, one or more scanning parameters for each of the plurality of regions may be determined based on the plurality of protocols, and one or more stitching parameters between protocols corresponding to each pair of neighboring regions of the plurality of regions may be determined. Exemplary scanning parameters for each of the plurality of regions may relate to spatial information, pulse sequences, weighting schemes, and/or distortion rectifications of the region. Exemplary stitching parameters may include a positional relationship of each pair of neighboring regions, stitching algorithms, rectification algorithms, relative positions of images corresponding to each pair of neighboring regions of the plurality of regions, etc. In some embodiments, the operation 820 may be similar to or the same as the operation 620 of the process 600 as illustrated in FIG. 6, the description of which is not repeated here.

In 830, at least one of the one or more scanning parameters of at least one region or the one or more stitching parameters between protocols corresponding to at least one pair of neighboring regions may be adjusted according to a parameter adjustment instruction, and/or at least one protocol may be added into or deleted from the plurality of protocols according to a protocol modification instruction.

In some embodiments, the parameter adjustment instruction and/or the protocol modification instruction may be obtained from a user (e.g., a doctor, a technician, etc.). In some embodiments, the user may adjust the at least one of the one or more scanning parameters of at least one region or the one or more stitching parameters between protocols corresponding to at least one pair of neighboring regions through a user interface, such as, the terminal device 140, the I/O module 330, etc. In some embodiments, the user may add into or delete from the plurality of protocols the at least one protocol according to actual situations through the user interface. For example, if the subject is much taller than an ordinary person, an additional region may need to be added to the plurality of regions such that the whole spine of the subject may be scanned. Accordingly, a protocol corresponding to the addition region may be added into the plurality of protocols. After the protocol is added into the plurality of protocols, one or more scanning parameters of the region and one or more stitching parameters corresponding to the region and a neighboring region may be determined.

In some embodiments, the parameter adjustment instruction and/or the protocol modification instruction may be obtained from the one or more components of the imaging system 100, for example, the verification module 530. For example, if the image stitching verification data generated in 630 indicates that at least one of the parameters to be verified does not satisfy one or more of the at least one group of image stitching conditions, the processing device 120 (e.g., the verification module 530) may generate the parameter adjustment instruction for adjusting at least one of the parameters to be verified. As another example, if the image stitching verification data generated in 630 indicates that at least one of the parameters to be verified does not satisfy one or more of the at least one group of image stitching conditions, the processing device 120 (e.g., the verification module 530) may generate the protocol modification instruction for adding into or deleting from the plurality of protocols at least one protocol.

In 840, image stitching verification data associated with the plurality of regions may be generated based on the adjusted at least one of the one or more scanning parameters of the at least one region, the adjusted one or more stitching parameters corresponding to the at least one pair of neighboring regions, and/or protocols after the at least one protocol is added into or deleted from the plurality of protocols.

After the at least one of the parameters to be verified is adjusted according to the parameter adjustment instruction, and/or the at least one protocol is added into or deleted from the plurality of protocols according to the protocol modification instruction, the parameters to be verified and/or the protocols determined in 820 may be updated. The image stitching verification data associated with the plurality of regions may be generated based on the updated parameters to be verified and/or updated protocols. In some embodiments, the operation 840 for generating the image stitching verification data may be similar to or the same as the operation 630 of the process 600 illustrated in FIG. 6, the description of which is not repeated here. In some embodiments, the operation 840 for generating the image stitching verification data may be performed according to the process 700 as illustrated in FIG. 7, the description of which is not repeated here.

In 850, the scanner may be directed to scan the subject based at least in part on the image stitching verification data. In some embodiments, the operation 850 for directing the scanner to scan the subject may be similar to or the same as the operation 640 of the process 600 as illustrated in FIG. 6, the description of which is not repeated here.

In some embodiments, if the image stitching verification data indicates that the image of the subject can be generated, the scanner 110 may be directed to scan the plurality of regions of the subject according to the plurality of protocols, respectively. In some embodiments, the information that the image of the subject can be generated may be provided to the user, and the user may be prompted to initiate the scanner 110 to scan the plurality of regions. The information that the image of the subject can be generated may be provided to the user in various ways, which is not limiting. For example, a prompting box, a status icon, and/or text that may indicate the image of the subject can be generated may be presented to the user through a user interface.

In some embodiments, if the image stitching verification data indicates that the image of the subject can not be generated, the information that the image of the subject can not be generated may be provided to the user, and the reason that the image of the subject can not be generated may also be provided to the user simultaneously. In some embodiments, the processing device 120 may further generate a parameter adjustment recommendation for adjusting the parameters to be verified.

By obtaining and resolving a plurality of protocols corresponding to a plurality of regions, one or more scanning parameters for each of the plurality of regions may be determined based on the plurality of protocols, and one or more stitching parameters between protocols corresponding to each pair of neighboring regions of the plurality of regions may be determined. Before an imaging scan is performed on the plurality of regions, image stitching verification data regarding whether the images of each region can be reconstructed and stitched may be performed in advance. A user may be prompted with the image stitching verification data. In this way, the imaging scan process may be optimized, the success rate of the image stitching may be improved, and the probability of repetitive scannings may be reduced, thereby reducing the time for scanning a patient in the imaging scan, and being more friendly to doctors and patients.

FIG. 9 includes a flowchart illustrating an exemplary process for generating an image of a subject according to some embodiments of the present disclosure. In some embodiments, the process 900 may be executed by the imaging system 100. For example, the process 900 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 900.

In 910, a plurality of protocols for scanning a subject using a scanner may be obtained, the plurality of protocols corresponding to a plurality of regions of the subject, respectively. A protocol corresponding to a region may include a certain number of pulse sequences oriented in different planes and/or with different parameters. The protocol may also include information regarding image contrast and/or ratio, an ROI, slice thickness, a weighting scheme (e.g., T1 weighted, T2 weighted, proton density weighted, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a count or number of images, direction of the images, or the like, or any combination thereof.

The plurality of protocols may be obtained from a storage device (e.g., the storage device 130, the storage 320, the storage 490, cloud storage, etc.). For example, the obtaining module 510 may retrieve the plurality of protocols from a database including protocols of various parameters stored in the storage device. The plurality of protocols may be retrieved from the database according to an instruction of a user (e.g., a doctor, a technician, etc.), default settings of the imaging system 100, etc.

In some embodiments, the operation 910 may be similar to or the same as the operation 610 of the process 600 as illustrated in FIG. 6, and the description of which is not repeated here.

In 920, one or more stitching parameters between protocols corresponding to each pair of neighboring regions of the plurality of regions may be determined.

Exemplary stitching parameters may include a positional relationship of each pair of neighboring regions, stitching algorithms, rectification algorithms, relative positions of images corresponding to each pair of neighboring regions of the plurality of regions, etc. The positional relationship of each pair of neighboring regions may include an inclusion relationship, a completely overlapping relationship, a partially overlapping relationship, an abutting relationship, and/or a noncontiguous relationship.

In some embodiments, the operation 920 may be similar to or the same as a portion of the operation 620 of the process 600 as illustrated in FIG. 6, and the description of which is not repeated here.

In 930, image stitching verification data associated with the plurality of regions may be generated based at least in part on the one or more stitching parameters between protocols corresponding to each pair of neighboring regions of the plurality of regions.

The image stitching verification data may include data indicating the feasibility of generating a stitched image of the subject (i.e., whether a stitched image of the subject can be generated by stitching images of the plurality of regions). In some embodiments, the image stitching verification data may relate to at least one group of image stitching conditions. In some embodiments, the image stitching verification data may be generated by determining whether the one or more stitching parameters between protocols corresponding to each pair of neighboring regions of the plurality of regions satisfy the at least one group of image stitching conditions.

In some embodiments, the image stitching verification data may be generated by determining whether imaging parameters of the plurality of regions are consistent, and/or whether spatial parameters corresponding to images of each pair of neighboring regions satisfy a spatial stitching condition. The determinations or at least a part thereof may constitute the at least one group of image stitching conditions. In some embodiments, the determination as to whether the imaging parameters of the plurality of regions are consistent may be made based at least in part on the one or more stitching parameters between protocols corresponding to each pair of neighboring regions of the plurality of regions. The determination as to whether spatial parameters corresponding to images of each pair of neighboring regions satisfy a spatial stitching condition may also be made based at least in part on the one or more stitching parameters between protocols corresponding to each pair of neighboring regions of the plurality of regions. It should be noted that the order in which the determinations are made and/or the content of the determinations are not limited to what is expressly exemplified in the present disclosure. In some embodiments, the content of the determinations may be adjusted according to actual needs. For example, the content of the determinations may vary if the scanner is a CT scanner, a PET scanner, a PET-CT scanner, or a PET-MR scanner.

The imaging parameters for imaging a region of the subject may be associated with, for example, sequence types, weighting schemes, distortion rectifications, etc.

The spatial stitching condition may relate to each pair of neighboring regions of the plurality of regions. In some embodiments, the regional stitching condition corresponding to a pair neighboring regions may relate to an inclusion relationship, a partially overlapping relationship, an image angle condition, etc.

More details regarding the generation of the image stitching verification data may be found elsewhere in the present disclosure. See, for example, FIG. 7 and the descriptions thereof.

In 940, the scanner may be directed to scan the subject based at least in part on the image stitching verification data.

In some embodiments, the image stitching verification data may be output to a user (e.g., a doctor, a technician, etc.). For example, the image stitching verification data may be displayed on a display interface of a terminal device (e.g., a desktop, a laptop, the mobile device 400, etc.). In some embodiments, if the image stitching verification data indicates that the parameters to be verified satisfy the at least one group of image stitching conditions (i.e., the image stitching may succeed), the scanner 110 may be directed to scan the plurality of regions according to the plurality of protocols, respectively. After the plurality of regions of the subject are scanned, scanning data of the plurality of regions generated by the scanner may be obtained. Images of each of the plurality of regions of the subject may be reconstructed based on the scanning data. A stitched image of the entire subject may be generated by stitching, according to the one or more stitching parameters between protocols corresponding to each pair of neighboring regions, the reconstructed images of the plurality of regions.

In some embodiments, if the image stitching verification data indicates that at least one of the one or more stitching parameters between protocols corresponding to the identified pair of neighboring regions does not satisfy one or more of the at least one group of image stitching conditions (i.e., the image stitching may fail), the imaging system 100 may identify a pair of neighboring regions in which an error exists in at least one of the one or more stitching parameters between protocols corresponding to the pair of neighboring regions. The imaging system 100 may generate a parameter adjustment recommendation for adjusting the at least one of the one or more stitching parameters between protocols corresponding to the identified pair of neighboring regions. In some embodiments, the information output may include information relating to the identified pair of neighboring regions, the error existed in the at least one of the one or more stitching parameters between protocols corresponding to the pair of neighboring regions, and/or the parameter adjustment recommendation through, e.g., the display interface of the terminal device.

It should be noted that the above description of the process 900 is merely provided for the purposes of illustration, not intended to limit the scope of the present disclosure. For persons having ordinary skills in the art, multiple variations and modifications may be made under the teachings of the present disclosure. For example, the process 900 may further include an operation for determining one or more scanning parameters for each of the plurality of regions based on the plurality of protocols. The image stitching verification data associated with the plurality of regions may be generated based on at least one of the one or more scanning parameters of each region and the one or more stitching parameters between protocols corresponding to each pair of neighboring regions of the plurality of regions. However, those variations and modifications may not depart the spirit and scope of this disclosure.

Figure 10:
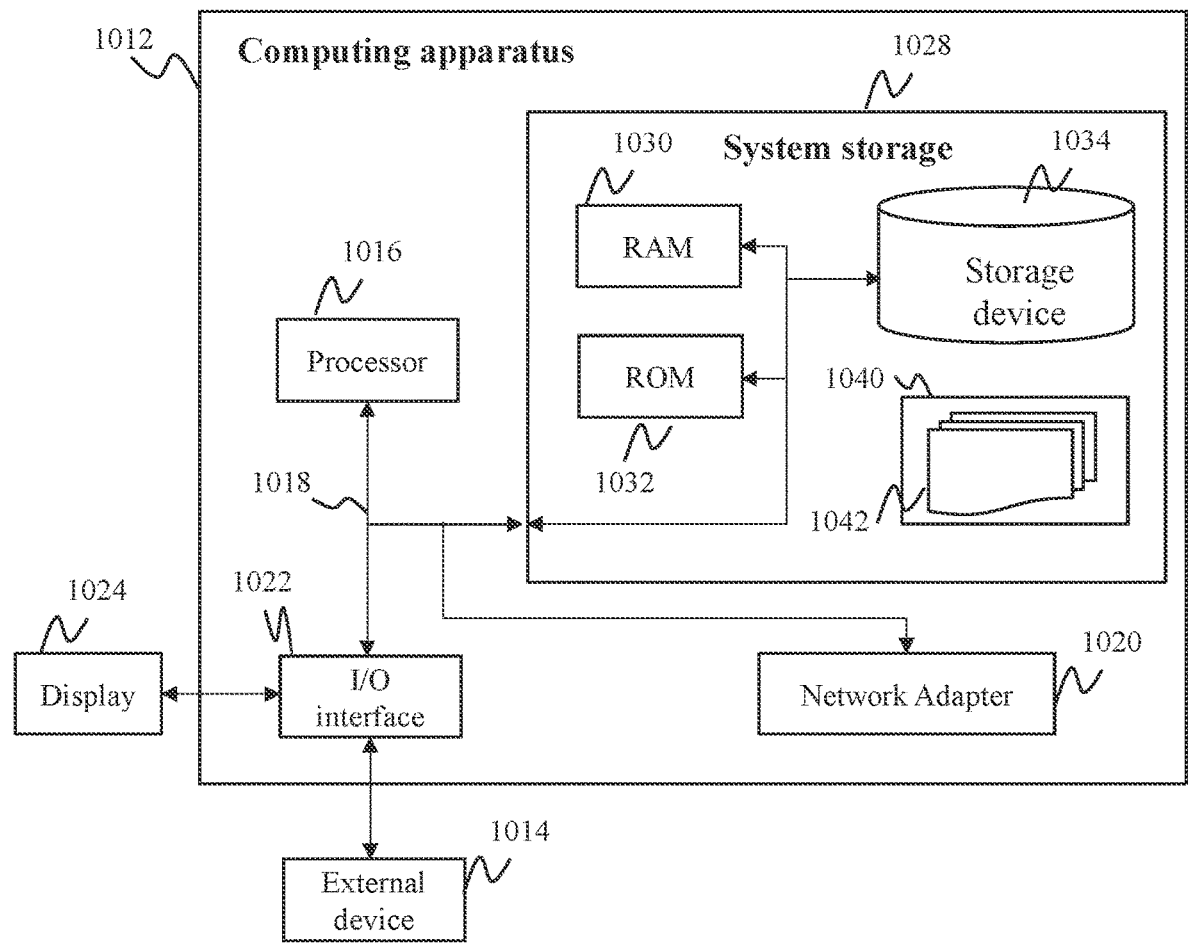
FIG. 10 is a schematic diagram of an exemplary computing apparatus according to some embodiments of the present disclosure.

FIG. 10 is a schematic diagram of an exemplary computing apparatus according to some embodiments of the present disclosure. The computing apparatus 1012 may facilitate the implementation of the processes or operations provided in the present disclosure. The computing apparatus 1012 illustrated in FIG. 10 is merely an example, but not intended to limit the scope of the present disclosure.

As shown in FIG. 10, the computing apparatus 1012 may be implemented by a computing device of general purposes. The computing apparatus 1012 may include but are not limited to one or more processors 1016, a system memory 1028, and a bus 1018 that connects elements or components of the computing apparatus 1012, such as the system memory 1028, the one or more processors 1016, etc.

The bus 1018 may represent one or more of several types of bus structures, including a memory bus, a memory controller, peripheral bus, an accelerated graphics port, the one or more processors 1016, or a local bus using any of a variety of bus structures. For example, the bus structures may include but not limited to, an Industry Standard Architecture (ISA) bus, a Micro Channel Architecture (MAC) bus, an Enhanced ISA Bus, a Video Electronics Standards Association (VESA) local bus, a peripheral component interconnects (PCI) bus, etc.

The computing apparatus 1012 may include a variety of computer readable media. The computer readable media may be any available media including volatile or non-volatile media, removable or non-removable media, etc., that may be accessible by the computing apparatus 1012.

The system memory 1028 may include computer readable media in a form of volatile memory, for example, a random access memory (RAM) 1030 and/or a read-only memory (ROM) 1032. The computing apparatus 1012 may further include other removable/non-removable or volatile/non-volatile computer system storage media. Merely by ways of example, a storage device 1034 may be non-removable, non-volatile magnetic media (not shown in the figure, commonly referred to as a "hard disk drive") for reading and writing. Although not shown in FIG. 10, a disk drive for reading and writing to a removable non-volatile disk (such as a "floppy disk") and a removable non-volatile disk (such as a CD-ROM, a DVD-ROM, or other optical media) may be provided. In these cases, each drive may be coupled to the bus 1018 via one or more data medium ports. The system memory 1028 may include at least one program product having a set (e.g., at least one) of program modules configured to implement the functions provided in the above embodiments of the present disclosure.

A program/utility tool 1040 having a set (at least one) of program modules 1042, which may be stored, for example, in the system memory 1028. The program modules 1042 may include but not limited to, an operating system, one or more applications, other program modules, or program data. Each or a combination of one or more of the above listed program modules may have a network environment implementation. The program module 1042 may perform the functions and/or methods provided in the described embodiments of the present disclosure.

The computing apparatus 1012 may also be in communication with one or more external devices 1014 (e.g., a keyboard, a pointing device, a display 1024, etc.), one or more devices that enable a user to interact with the computing apparatus 1012, and/or any devices (e.g., a network card, a modem, etc.) that enable the computing apparatus 1012 to communicate with one or more other computing devices. The communication may be realized via an input/output (I/O) interface 1022. Also, the computing apparatus 1012 may also communicate with one or more networks (e.g., a local area network (LAN), a wide area network (WAN), and/or a public network, such as the Internet) through a network adapter 1020. As shown in the figure, the network adapter 1020 may communicate with other modules of computing apparatus 1012 via the bus 1018. It should be understood that, other hardware and/or software modules may be utilized in combination with the computing apparatus 1012, including but not limited to microcode, device drivers, redundant processing units, external disk drive arrays, RAID systems, Tape drives, or data backup storage systems.

The one or more processors 1016 may implement, by running a program stored in the system memory 1028, various functional applications and/or data processing, for example, a method of generating an image of a subject provided in some embodiments of the present disclosure. According to an aspect of the present disclosure, a plurality of protocols for scanning a subject using a scanner may be obtained, the plurality of protocols corresponding to a plurality of regions of the subject, respectively. One or more scanning parameters for each of the plurality of regions may be determined based on the plurality of protocols, and one or more stitching parameters between protocols corresponding to each pair of neighboring regions of the plurality of regions may be determined. Image stitching verification data associated with the plurality of regions may be generated based on at least one of the one or more scanning parameters of each region and the one or more stitching parameters between protocols corresponding to each pair of neighboring regions of the plurality of regions. The scanner may be directed to scan the subject based at least in part on the image stitching verification data.

Those skilled in the art may understand that the one or more processors 1016 may also implement technical solutions of the exposure process control method provided by any embodiments of the present disclosure.

The present disclosure may further provide a computer readable storage medium storing computer programs. When the computer programs are executed by a processor, operations of generating an image of a subject provided in the present disclosure may be implemented. According to an aspect of the present disclosure, a plurality of protocols for scanning a subject using a scanner may be obtained, the plurality of protocols corresponding to a plurality of regions of the subject, respectively. One or more scanning parameters for each of the plurality of regions may be determined based on the plurality of protocols, and one or more stitching parameters between protocols corresponding to each pair of neighboring regions of the plurality of regions may be determined. Image stitching verification data associated with the plurality of regions may be generated based on at least one of the one or more scanning parameters of each region and the one or more stitching parameters between protocols corresponding to each pair of neighboring regions of the plurality of regions. The scanner may be directed to scan the subject based at least in part on the image stitching verification data.

It should be noted that the computer programs stored in the computer readable storage medium may not limited to the methods or operations provided above, other methods or operations related to the automated positioning of the subject may also be provided.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device including a set of instructions; and
at least one processor configured to communicate with the at least one storage device, wherein when the set of instructions is executed by the processor, cause the at least one processor to perform operations including:
obtaining a plurality of protocols for scanning a subject using a scanner, wherein the plurality of protocols correspond to a plurality of regions of the subject, respectively;
determining one or more stitching parameters between protocols corresponding to each pair of neighboring regions of the plurality of regions;
generating image stitching verification data associated with the plurality of regions based at least in part on at least one of the one or more stitching parameters between protocols corresponding to each pair of neighboring regions of the plurality of regions; and directing the scanner to scan the subject based at least in part on the image stitching verification data.

2. The system of claim 1, wherein the image stitching verification data relates to at least one group of image stitching conditions, the generating image stitching verification data including:

determining whether the one or more stitching parameters between protocols corresponding to each pair of neighboring regions satisfy the at least one group of image stitching conditions.

3. The system of claim 2, wherein the directing the scanner to scan the subject based at least in part on the image stitching verification data includes:

directing the scanner to scan the plurality of regions of the subject according to the plurality of protocols, respectively, in response to determining that the one or more stitching parameters between protocols corresponding to each pair of neighboring regions satisfy the at least one group of image stitching conditions.

4. The system of claim 3, the operations further including:

obtaining scanning data of the plurality of regions of the subject generated by the scanner;

reconstructing one or more images of each of the plurality of regions of the subject based on the scanning data; and generating an image of the subject by stitching, according to the one or more stitching parameters between protocols corresponding to each pair of neighboring regions, the one or more reconstructed images of each of the plurality of regions.

5. The system of claim 2, wherein the directing the scanner to scan the subject based at least in part on the image stitching verification data includes:

identifying a pair of neighboring regions in which an error exists in at least one of the one or more stitching parameters between protocols corresponding to the pair of neighboring regions; and generating a parameter adjustment recommendation for adjusting at least one of the one or more stitching parameters between protocols corresponding to the identified pair of neighboring regions, in response to determining that the at least one of the one or more stitching parameters between protocols corresponding to the identified pair of neighboring regions do not satisfy one or more of the at least one group of image stitching conditions.

6. The system of claim 2, the determining whether the one or more stitching parameters between protocols corresponding to each pair of neighboring regions satisfy the at least one group of image stitching conditions includes at least one of:

determining whether imaging parameters of the plurality of regions are consistent, or determining whether spatial parameters corresponding to images of each pair of neighboring regions satisfy a spatial stitching condition.

7. The system of claim 6, wherein the determining whether the imaging parameters of the plurality of regions are consistent includes:

determining whether at least one of sequence types, weighting schemes, or distortion rectifications of the plurality of regions are consistent.

8. The system of claim 6, wherein the determining whether spatial parameters corresponding to images of each pair of neighboring regions satisfy a spatial stitching condition includes:

determining whether an image of a region is included in an image of another region among the plurality of regions, determining whether images of each pair of neighboring regions at least in part overlap, or determining whether an angle between images of each pair of neighboring regions satisfies an image angle condition.

9. The system of claim 1, the operations further including:

obtaining a parameter adjustment instruction from a user; and adjusting at least one of the one or more stitching parameters between protocols corresponding to at least one pair of neighboring regions according to the parameter adjustment instruction.

10. The system of claim 1, the operations further including:

obtaining a protocol modification instruction from a user; and modifying at least part of the plurality of protocols according to the protocol modification instruction.

11. The system of claim 10, wherein the modifying at least part of the plurality of protocol includes:

adding into or deleting from the plurality of protocols at least one protocol.

12. The system of claim 1, the operations further including:

determining one or more scanning parameters for each of the plurality of regions based on the plurality of protocols; and generating the image stitching verification data associated with the plurality of regions based further on at least one of the one or more scanning parameters for each of the plurality of regions.

13. A system, comprising:

at least one storage device including a set of instructions; and at least one processor configured to communicate with the at least one storage device, wherein when the set of instructions is executed by the processor, cause the at least one processor to perform operations including:

obtaining a plurality of protocols for scanning a subject using a scanner, wherein the plurality of protocols correspond to a plurality of regions of the subject, respectively;

determining one or more scanning parameters for each of the plurality of regions based on the plurality of protocols;

determining one or more stitching parameters between protocols corresponding to each pair of neighboring regions of the plurality of regions;

generating image stitching verification data associated with the plurality of regions based on at least one of the one or more scanning parameters of each region and the one or more stitching parameters between protocols corresponding to each pair of neighboring regions of the plurality of regions; and directing the scanner to scan the subject based at least in part on the image stitching verification data.

14. A method implemented on a computing device having a processor and a computer-readable storage device, the method comprising:

obtaining a plurality of protocols for scanning a subject using a scanner, wherein the plurality of protocols correspond to a plurality of regions of the subject, respectively;

determining one or more stitching parameters between protocols corresponding to each pair of neighboring regions of the plurality of regions;

generating image stitching verification data associated with the plurality of regions based at least in part on at least one of the one or more stitching parameters between protocols corresponding to each pair of neighboring regions of the plurality of regions; and directing the scanner to scan the subject based at least in part on the image stitching verification data.

15. The method of claim 14, wherein the image stitching verification data relates to at least one group of image stitching conditions, the generating image stitching verification data including:

determining whether the one or more stitching parameters between protocols corresponding to each pair of neighboring regions satisfy the at least one group of image stitching conditions.

16. The method of claim 15, wherein the directing the scanner to scan the subject based at least in part on the image stitching verification data includes:

directing the scanner to scan the plurality of regions of the subject according to the plurality of protocols, respectively, in response to determining that the one or more stitching parameters between protocols corresponding to each pair of neighboring regions satisfy the at least one group of image stitching conditions.

17. The method of claim 16, further including:

obtaining scanning data of the plurality of regions of the subject generated by the scanner;

reconstructing one or more images of each of the plurality of regions of the subject based on the scanning data; and generating an image of the subject by stitching, according to the one or more stitching parameters between protocols corresponding to each pair of neighboring regions, the one or more reconstructed images of each of the plurality of regions.

18. The method of claim 15, wherein the directing the scanner to scan the subject based at least in part on the image stitching verification data includes:

identifying a pair of neighboring regions in which an error exists in at least one of the one or more stitching parameters between protocols corresponding to the pair of neighboring regions; and generating a parameter adjustment recommendation for adjusting at least one of the one or more stitching parameters between protocols corresponding to the identified pair of neighboring regions, in response to determining that the at least one of the one or more stitching parameters between protocols corresponding to the identified pair of neighboring regions do not satisfy one or more of the at least one group of image stitching conditions.

19. The method of claim 15, the determining whether the one or more stitching parameters between protocols corresponding to each pair of neighboring regions satisfy the at least one group of image stitching conditions includes at least one of:

determining whether imaging parameters of the plurality of regions are consistent, or determining whether spatial parameters corresponding to images of each pair of neighboring regions satisfy a spatial stitching condition.

20. The method of claim 19, wherein the determining whether the imaging parameters of the plurality of regions are consistent includes:

determining whether at least one of sequence types, weighting schemes, or distortion rectifications of the plurality of regions are consistent.

* * * * *